(12) United States Patent
Macatangay et al.

(10) Patent No.: US 8,002,749 B2
(45) Date of Patent: Aug. 23, 2011

(54) VALVE ASSEMBLY

(75) Inventors: Edwin E. Macatangay, Ellettsville, IN (US); William L. Howat, Bloomington, IN (US)

(73) Assignee: Cook Medical Technologies LLC, Bloomington, IN (US)

(*) Notice: Subject to any disclaimer, the term of this patent is extended or adjusted under 35 U.S.C. 154(b) by 392 days.

(21) Appl. No.: 11/966,385

(22) Filed: Dec. 28, 2007

(65) Prior Publication Data
US 2008/0157017 A1 Jul. 3, 2008

Related U.S. Application Data

(60) Provisional application No. 60/878,232, filed on Jan. 3, 2007.

(51) Int. Cl.
| A61M 5/178 | (2006.01) |
| A61M 5/00 | (2006.01) |
| A61M 5/14 | (2006.01) |
| A61M 25/16 | (2006.01) |
| A61M 25/18 | (2006.01) |
| A61M 39/00 | (2006.01) |
| A61M 39/10 | (2006.01) |

(52) U.S. Cl. ......... 604/167.03; 604/164.01; 604/164.02; 604/167.05; 604/167.06; 604/246; 604/248; 604/256; 604/533; 604/537

(58) Field of Classification Search ............. 604/167.03, 604/167.05, 533, 905, 164.01, 164.02, 167.01, 604/167.02, 167.06, 246, 248, 256, 537, 604/539, 167.04, 534, 535, 536; 251/314, 251/317
See application file for complete search history.

(56) References Cited

U.S. PATENT DOCUMENTS
4,292,969 A * 10/1981 Raible et al. ............ 604/250
(Continued)

FOREIGN PATENT DOCUMENTS
FR 2 863 504 A1 6/2005
(Continued)

OTHER PUBLICATIONS

International Search Report and Written Opinion mailed May 20, 2008, from International Application No. PCT/US2007/089059.

*Primary Examiner* — Theodore Stigell
*Assistant Examiner* — Shefali Patel
(74) *Attorney, Agent, or Firm* — Brinks Hofer Gilson & Lione

(57) ABSTRACT

A valve assembly includes a valve collar, a rotatable valve control member, and a flexible valve member disposed therebetween. The valve control member and the valve collar are aligned to define an elongated passageway, and the flexible valve member is disposed along the passageway. The valve collar is structured such that at least a portion thereof is capable of radial flexure upon engagement with a mechanism on the rotatable valve control member. One end of the valve member is secured to the valve collar, and the other end is secured to the rotatable valve control member. Upon rotation of the rotatable valve control member relative to the valve collar, the mechanism of the rotatable valve control member engages the valve collar portion in a manner such that the valve collar portion flexes in a radial direction and a tactile sensation is produced thereby, and the flexible valve member constricts from an open position to a position wherein the flexible valve member opening is at least partially closed to passage of fluid therethrough.

18 Claims, 5 Drawing Sheets

U.S. PATENT DOCUMENTS

| | | | |
|---|---|---|---|
| 4,540,411 A * | 9/1985 | Bodicky | 604/167.05 |
| 5,006,113 A | 4/1991 | Fischer | 604/167 |
| 5,158,553 A | 10/1992 | Berry et al. | 604/248 |
| 5,361,283 A * | 11/1994 | Attix | 376/446 |
| 6,416,499 B2 | 7/2002 | Paul, Jr. | 604/256 |
| 7,172,580 B2 | 2/2007 | Hruska et al. | 604/248 |
| 2005/0171479 A1 * | 8/2005 | Hruska et al. | 604/167.06 |
| 2006/0229564 A1 * | 10/2006 | Andersen et al. | 604/167.03 |
| 2007/0204924 A1 * | 9/2007 | Delgiacco et al. | 137/625.31 |

FOREIGN PATENT DOCUMENTS

WO     WO 03/048616 A1     6/2003

* cited by examiner

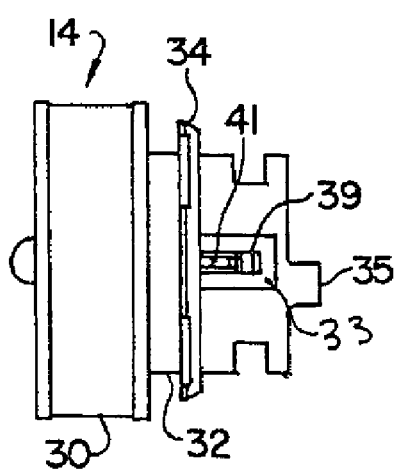
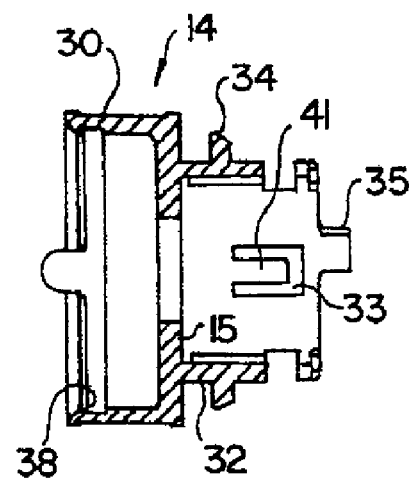
FIG. 4　　　　　　FIG. 5
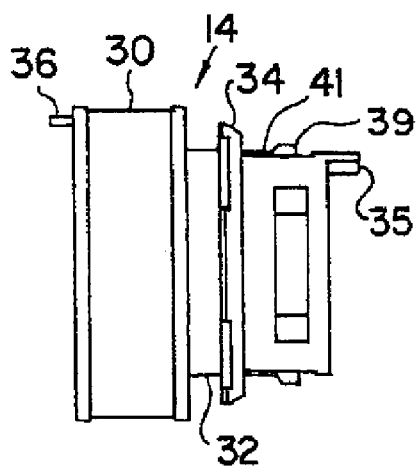
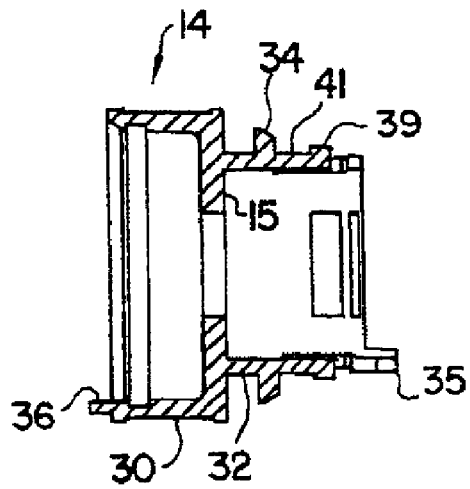
FIG. 6　　　　　　FIG. 7
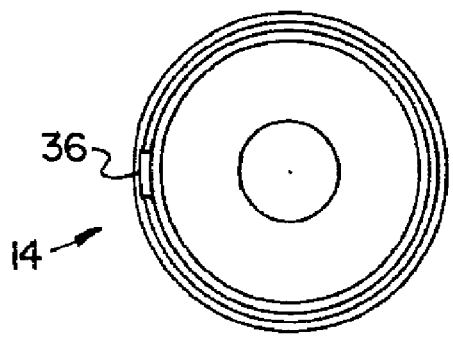
FIG. 8

VALVE ASSEMBLY

RELATED APPLICATION

The present patent document claims the benefit of the filing date under 35 U.S.C. §119(e) of Provisional U.S. Patent Application Ser. No. 60/878,232, filed Jan. 3, 2007, which is hereby incorporated by reference.

BACKGROUND

1. Technical Field

The present invention relates to a valve assembly for controlling the flow of fluids through a medical device, and more particularly, to a hemostatic valve assembly incorporating an iris valve for controlling fluid flow.

2. Background Information

A variety of well-known medical procedures are initiated by introducing an interventional device such as a catheter, trocar, sheath, and the like into a vessel in a patient's body. Typical procedures for introducing an interventional device into a blood vessel include the well-known Seldinger technique. In the Seldinger technique, a needle is injected into a blood vessel, and a wire guide is inserted into the vessel through a bore of the needle. The needle is withdrawn, and a dilator is inserted over the wire guide. The dilator is typically located inside an introducer sheath which is also inserted into the vessel. The introducer sheath typically includes a hemostatic valve, through which the dilator passes. Following proper placement of the introducer sheath, the dilator is removed. The interventional device may then be inserted through the sheath and hemostatic valve into the vessel.

As the interventional device is introduced into the vessel, care must be taken to avoid the undesirable introduction or leakage of air into the vessel. Similarly, care must be taken to avoid the undesirable leakage of blood or other bodily fluids, or a cavity-pressurizing gas from the patient. As procedures for introducing catheters and other interventional devices have become more widely accepted, the procedures associated with their use have become more diverse, and the variety of sizes and types of such introducer devices has grown dramatically. As a result, the risk of inward or outward leakage of fluids has increased, along with the necessity to maintain vigilance to minimize the possibility of such leakage.

One known way to minimize leakage is to provide one or more disk-like gaskets in an elongated passageway of a device through which fluids may be controllably passed into or out of the body. Such disks have opposing surfaces and often include one or more slits that extend partially across each of the surfaces and inwardly toward the interior of the disk. A generally axial opening is provided between the slits to provide a sealable path for insertion of an interventional device through the disks. Examples of such disks are described, e.g., in U.S. Pat. Nos. 5,006,113 and 6,416,499, incorporated by reference herein. These disks are generally effective for sealing large diameter devices, but may be less effective for sealing smaller diameter devices. This may be especially true when a smaller diameter device is introduced through a disk following the earlier passage of a larger diameter device.

Another type of valve that is presently used for sealing elongated passages in a medical device to prevent passage of fluids is commonly referred to as an iris valve. Iris valves are described, e.g., in U.S. Pat. Nos. 5,158,553 and 7,172,580, incorporated by reference herein. An iris valve may comprise a valve hub that is joined to a catheter-type device, and a knob that is rotatably engaged with the hub. An elastomeric sleeve having an elongated passageway therethrough is positioned in an opening through the interior of the valve body. The opposing axial ends of the elastomeric sleeve are joined to the hub and the rotatable knob, respectively. When the rotatable knob is rotated in a first direction, the passageway of the elastomeric sleeve is fully opened. When the knob is rotated in a second direction opposite the first direction, the elastomeric sleeve is twisted intermediate the two ends to effect closure of all or part of the elongated passageway.

Although the prior art iris valves are generally effective for sealing sheaths of certain sizes and compositions, such valves have certain shortcomings. For example, the manner of engaging the ends of the valve of the '553 patent to the respective hub and knob is less than optimal. Such ends are capable of disengagement, which destroys the ability of the valve to form a seal. In addition, the outer housing of the valve is not easily grasped by the physician during use.

The valve of the '580 patent has been found to be generally effective in many applications. This valve may include longitudinal grooves and corresponding ridges that cooperate during rotation of the knob relative to the hub to provide feedback to the physician of the amount of closure of the valve. The particular design of the valve is believed to have sufficient flex in the respective valve parts to enable the knob to be easily rotated relative to the hub. However, the outer contour of this valve is generally cylindrical, and does not provide an ergonomic surface that provides for optimal manipulation by the physician.

It would be desirable to provide a valve assembly that overcomes the problems associated with prior art iris valves.

SUMMARY

The problems of the prior art are addressed by the features of the present invention. In one form thereof, the present invention comprises a valve assembly for controlling a flow of fluid. The valve assembly includes a valve collar, a rotatable valve control member, and a flexible valve member having an opening therethrough. The rotatable valve control member and the valve collar are aligned to define an elongated passageway, and the flexible valve member is disposed along the passageway. The valve collar has a proximal end and a distal end, and is structured such that at least a portion of the proximal end is capable of radial flexure. The rotatable valve control member has a proximal end and a distal end, and includes an ergonomic outer surface. The rotatable valve control member distal end is engaged with the valve collar proximal end in a manner such that the valve control member is at least partially rotatable relative to the valve collar. The rotatable valve control member includes a mechanism for engagement with the valve collar portion upon rotation of the rotatable valve control member. The flexible valve member having a proximal end and a distal end. The valve member distal end is secured to the valve collar, and the valve member proximal end is secured to the rotatable valve control member. Upon rotation of the rotatable valve control member in a first direction relative to the valve collar, the mechanism of the rotatable valve control member engages the valve collar portion in a manner such that the valve collar portion flexes in a radial direction and a tactile sensation is produced thereby, and such that the flexible valve member longitudinal opening constricts from an open position to a position wherein the flexible valve member opening is at least partially closed.

In another form thereof, the present invention comprises a valve assembly for controlling a flow of fluid. The valve assembly comprises a valve chamber having a proximal end and a distal end, and a valve collar having a proximal end and a distal end. The valve collar distal end is engaged with the valve chamber proximal end. A proximal portion of the valve collar comprises at least one generally U-shaped cut-out defining a radial ridge portion capable of radial flexure. A rotatable valve control member having a proximal end and a distal end includes an ergonomically arranged outer surface. The outer surface comprises a gently curved outer contour from a smaller diameter proximal end to a larger diameter distal end, and farther comprises one or more external members disposed along the contour for facilitating grasping and control of the rotatable valve control member. The rotatable valve control member distal end is engaged with said valve collar proximal end in a manner such that the valve control member is at least partially rotatable relative to the valve collar. The rotatable valve control member includes at least one inner member sized and shaped for engagement with the valve collar ridge in a manner such that the ridge flexes during rotation of the valve control member relative to the valve collar. The valve chamber, valve collar and rotatable valve control member are aligned in the valve assembly to define an elongated passageway therethrough. A flexible valve member has a proximal end and a distal end, wherein the distal end is secured to the valve collar, and the proximal end is secured to the rotatable valve control member. The flexible valve member is disposed along the passageway and has a longitudinal opening therethrough. Upon rotation of the rotatable valve control member in a first direction relative to the valve collar, the inner member of the rotatable valve control member engages a respective valve collar ridge in a manner such that the valve collar portion flexes in a radial direction, and a tactile sensation is produced thereby, and such that the valve member longitudinal opening constricts from an open position to a position wherein the opening is at least partially closed.

BRIEF DESCRIPTION OF THE DRAWINGS

FIG. 4 is a side view of the valve collar;

FIG. 5 is a sectional view of the collar of FIG. 4;

FIG. 6 is another side view of the collar of FIG. 4 taken from another rotational orientation;

FIG. 7 is a sectional view of the collar of FIG. 6;

FIG. 8 is an end view of the distal end of collar 14;

DETAILED DESCRIPTION OF THE DRAWINGS AND THE PRESENTLY PREFERRED EMBODIMENTS

Figure 1:
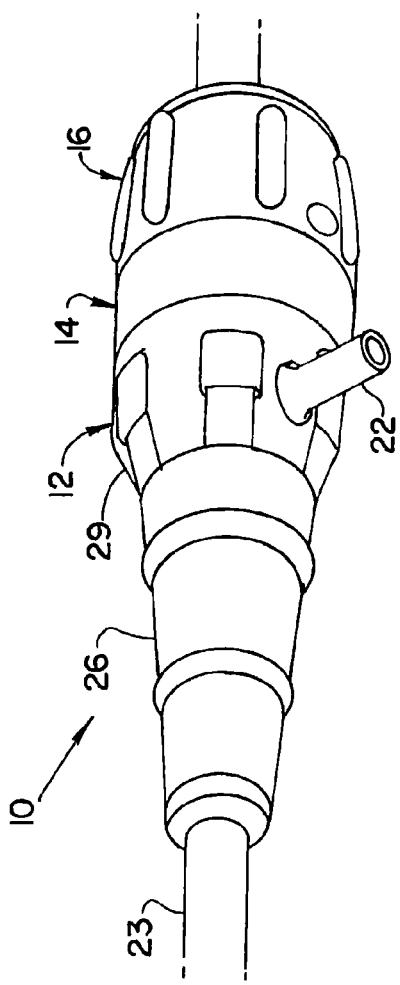
FIG. 1 is a perspective view of a hemostatic valve assembly according to an embodiment of the present invention.

For the purposes of promoting an understanding of the principles of the invention, reference will now be made to the embodiments illustrated in the drawings, and specific language will be used to describe the same. It should nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

In the following discussion, the terms "proximal" and "distal" will be used to describe the opposing axial ends of the valve assembly, as well as the axial ends of various components thereof. The term "proximal" is used in its conventional sense to refer to the end of the assembly (or component thereof) that is closest to the operator during use of the assembly. The term "distal" is used in its conventional sense to refer to the end of the assembly (or component thereof) that is initially inserted into the patient, or that is closest to the patient during use.

Figure 2:
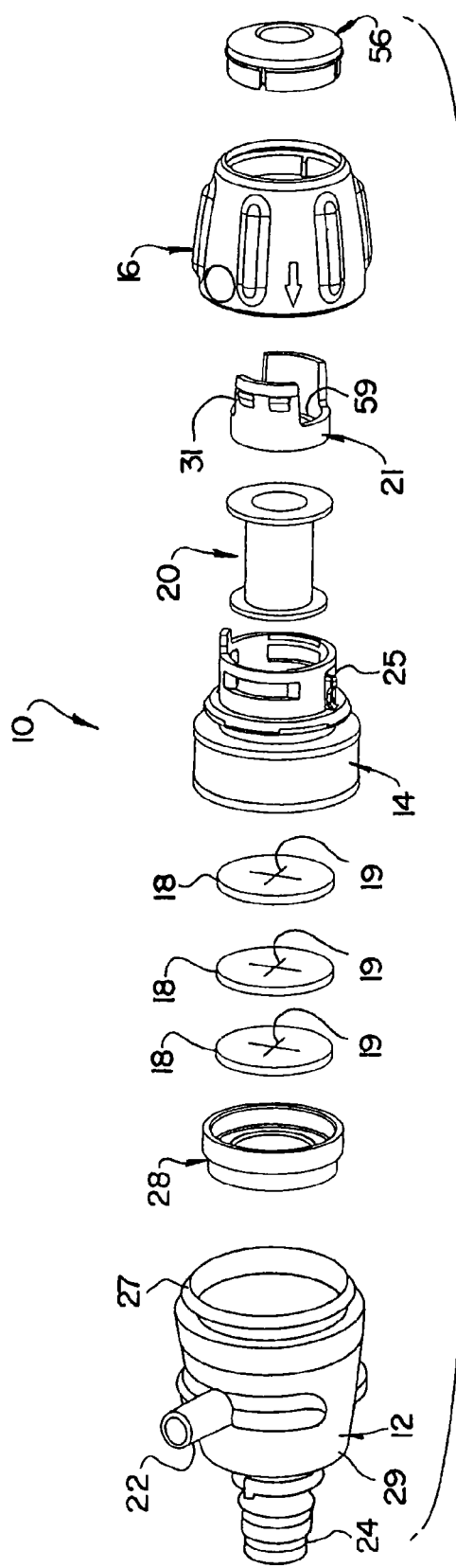
FIG. 2 is an exploded view of the hemostatic valve assembly of FIG. 1.
Figure 3:
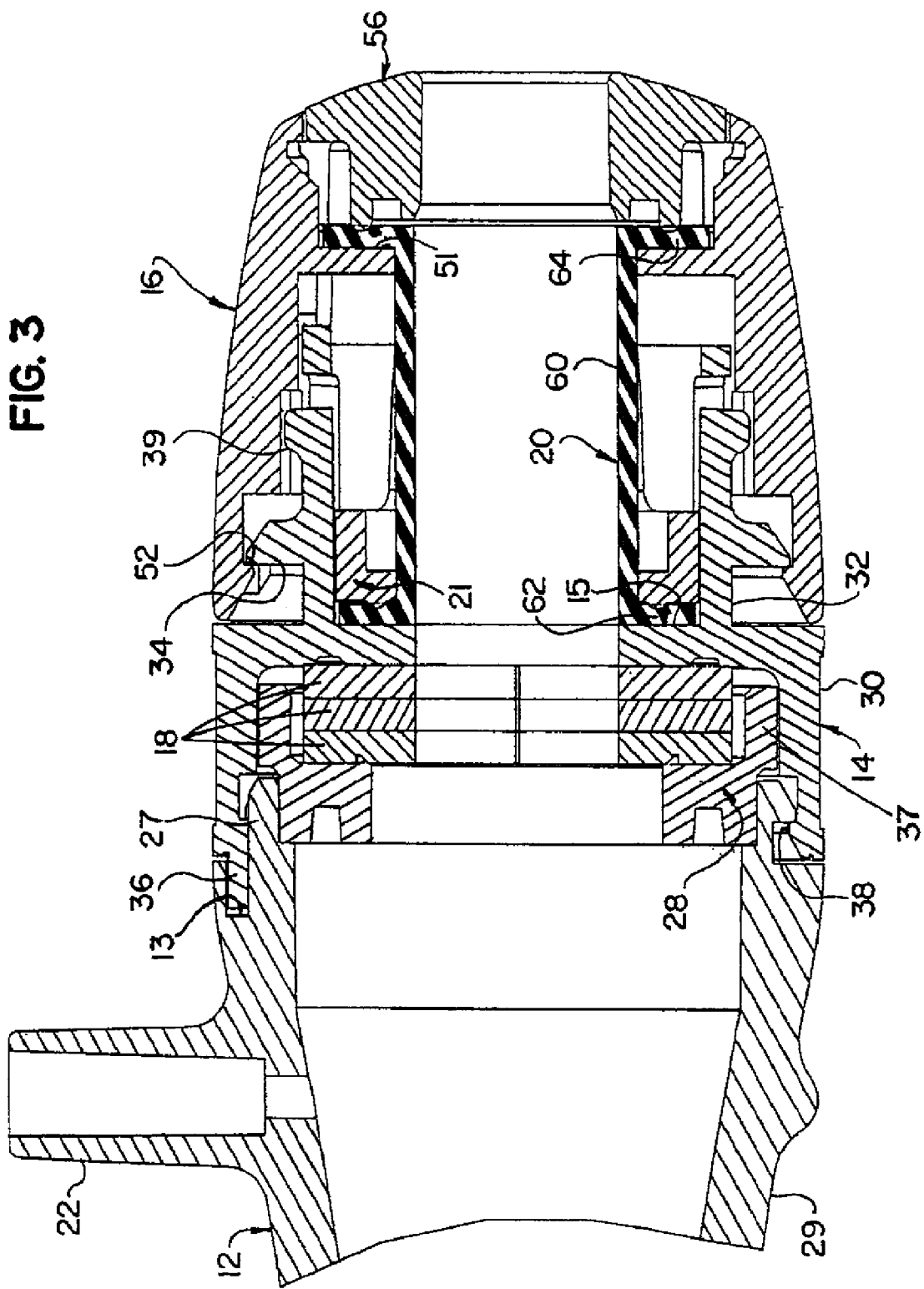
FIG. 3 is an enlarged longitudinal sectional view of a portion of the valve assembly of FIG. 1.
Figure 11:
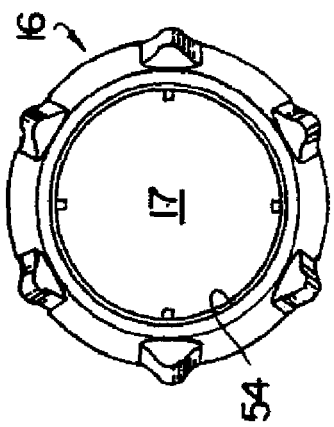
FIG. 11 is a proximal end view of the rotatable valve control member.
Figure 12:
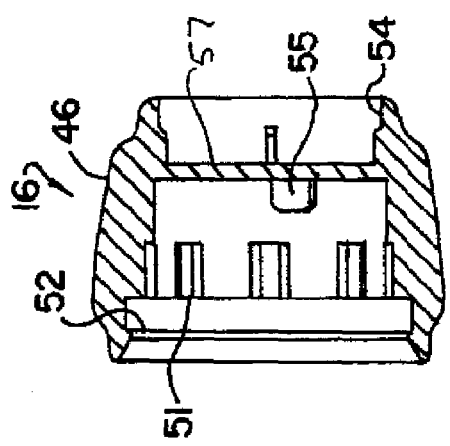
FIG. 12 is a sectional view of the rotatable valve control member as shown in FIG. 10.
Figure 10:
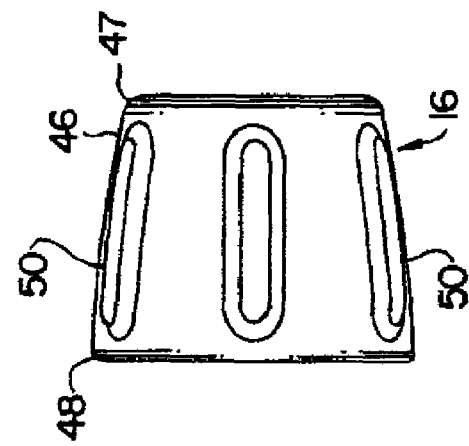
FIG. 10 is a side view of the rotatable valve control member.
Figure 9:
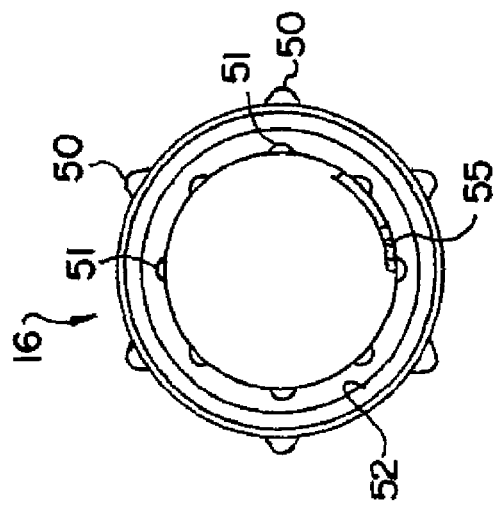
FIG. 9 is a distal end view of the rotatable valve control member.

FIG. 1 illustrates a perspective view of a hemostatic valve assembly 10 according to an embodiment of the present invention. FIG. 2 illustrates an exploded view of hemostatic valve assembly 10 of FIG. 1, and FIG. 3 is an enlarged longitudinal sectional view of a portion of the hemostatic valve assembly of FIG. 1.

In the preferred embodiment shown, hemostatic valve assembly 10 includes a valve chamber 12, a valve collar 14 and a rotatable valve control member 16. A check valve comprising one or more valve disks is disposed longitudinally between valve chamber 12 and valve collar 14. In the embodiment shown, the check valve comprises three longitudinally-aligned valve disks 18 (FIG. 2). A flexible valve sheath 20 of the "iris"-type is disposed between valve collar 14 and rotatable valve control member 16. Iris valves are known in the art and are described, for example, in the incorporated-by-reference U.S. Pat. Nos. 5,158,553 and 7,172,580. A collar seal 21 is provided to secure a flanged end of the iris valve to the valve collar 14. Collar seal 21 has an aperture 59 therethrough to receive an end of the iris valve. An end cap 56 is engaged, such as by a snap fit, to the proximal end of rotatable valve control member 16 to secure the other flanged end of the iris valve to rotatable valve control member 16.

Valve chamber 12 comprises an outer housing 29 having a side-arm spout 22 extending transversely therefrom. Spout 22 is sized and shaped for engagement with a tube or other device (not shown) for transmittal or drainage of a fluid or a drug in conventional fashion. In the preferred embodiment shown, proximal portion 27 of valve chamber 12 is sized for engagement by conventional means with the distal end of valve collar 14. The distal end of valve chamber 12 comprises a smaller diameter portion 24 for attaching valve assembly 10 to a device, such as introducer sheath 23 (FIG. 1), in conventional fashion. Introducer sheath 23 is provided for delivering a fluid medicament or a medical device to a target area in the body of the patient in well known fashion. Preferably a tapered outer member 26 is provided to improve the ergonomics of the device, and to provide strain relief in well known fashion.

Valve disks 18 are preferably conventional disk-type valves. Such valve disks are commercially available, for example, from Cook Incorporated, of Bloomington, Ind., under the trademark CHECK-FLO® valves. Valve disks 18 include one or more slits 19 sized for passage of an interventional device (not shown) therethrough. Preferably, valve disks 18 have a slit on each face thereof. The slits may extend either partially or fully through the disk. Valve disks of this type are well known in the art, and need not be further described herein. Preferably, three valve disks are stacked and arranged such that the slits are aligned as shown in FIG. 2. However, those skilled in the art will appreciate that other numbers of disks may be utilized, and the alignment of the slits in the disks need not be as shown in the figures. Preferably, a complementary-shaped ring member 28 (FIG. 2) has a channeled or otherwise shaped surface 37 (FIG. 3) for receiving at least the distal most one of disks 18.

A preferred embodiment of valve collar 14 is shown in greater detail in FIGS. 4-8. Valve collar 14 includes a larger diameter generally cylindrical portion 30, and a smaller diameter generally cylindrical portion 32 extending in the proximal direction from large diameter portion 30. Preferably an external snap ring 34 projects radially outwardly from smaller diameter portion 32 for engagement with complementary structure of rotatable valve control member 16. In the preferred embodiment shown, an internal snap ring 38 (FIGS. 3, 5) projects radially inwardly from large diameter portion 30 for engagement with valve chamber 12. A finger 36 projects axially in the distal direction from valve collar 14 and is received in cooperating slot 13 in valve chamber 12 for locking valve chamber 12 and valve collar 14 together in a manner such that relative rotation between the valve chamber and the valve collar is precluded.

In the preferred embodiment shown, valve collar smaller diameter 32 includes one or more U-shaped cut-outs 33 along its surface. U-shaped cut-outs 33 are sized and shaped to define a bridge 41. Bridge 41 extends generally in the proximal direction from surface 15 of valve collar 14, and terminates in outer ridge 39, Outer ridge 39 extends radially from bridge 41, and is capable of flexing inwardly into the bore of the collar, in a manner to be described. In this embodiment, each bridge 41 is only supported on one side, with the other three sides defined by the U-shaped cut-out 33.

A preferred embodiment of rotatable valve control member 16 is illustrated in greater detail in FIGS. 9-12. Rotatable valve control member 16 includes a body 46 having a gentle curved configuration from a smaller diameter proximal end 47 to a larger diameter distal end 48. Providing a curved outer configuration to the rotatable valve control member yields a more ergonomic outer surface than found in prior art designs that may include a substantially cylindrical outer surface. As a result, the physician may more easily grasp and control the device.

In the preferred embodiment shown, valve control member 16 also includes a plurality of optional ribs 50 spaced on the outer surface of body 46 along the gentle curvature. Ribs 50 provide additional ergonomic benefits to facilitate grasping and control by the physician. The embodiment shown in the drawings includes six ribs equally spaced along the outer surface of body 46. Those skilled in the art will appreciate that the number and spacing of ribs 50 is exemplary only, and that any number and spacing of ribs may be substituted. In addition, ribs 50 may have a multitude of possible cross-sectional shapes, and need not be positioned in generally linear fashion as shown. Rather, any configuration that provides an ergonomic benefit may be substituted. As an alternative to ribs, the outer body surface may be provided with one or more other known ergonomic surfaces, such as nubs, grooves, and the like. Those skilled in the art are readily capable of providing satisfactory alternative ergonomic mechanisms.

Rotatable valve control member 16 also preferably includes a plurality of members, such as ribs 51, disposed along an inner surface of the valve control member. Ribs 51 are configured to engage outer ridges 39 of collar 14 during use of the device, in a manner to be described. In the embodiments shown, eight ribs 51 are provided along the control member inner surface. Those skilled in the art will appreciate that this number is exemplary only, and that more, or fewer, ribs may be substituted. In addition, ribs 51 need not necessarily have the shape as illustrated herein, and other members that are engageable with outer ridges 39 may be substituted.

For rotation of rotatable valve control member 16 relative to collar 14, the operator rotates and applies a torque to rotatable valve control member 16. During rotation, inner ribs 51 of control member 16 engage respective outer ridges 39 of collar 14, thereby flexing bridge 41 and outer ridge 39 inwardly into the interior space of the valve. Upon such engagement and flexure, the outer ridge acts in a ratcheting manner, such that a tactile click-type sensation can be felt by the physician upon flexure of the outer ridge resulting from engagement with a respective rib 51. As control member 16 is further rotated, each rib 51 will successively engage successive outer ridges 39, thereby providing the physician with successive tactile sensations that correspond to the amount of rotation, and closure, of the valve that has taken place. In the preferred design having eight ribs 51, each one-eighth rotation of control member 16 results in an engagement with an outer ridge 39, thereby producing the tactile click that can be felt by the physician.

Although some prior art devices have included ratcheting mechanisms in valve devices, such devices have typically required that the rotatable member, and/or the collar member, have only a minimal thickness, and a generally cylindrical outer body. As a result, the members are capable of flexing relative to one another when the respective ratcheting mechanisms engage, thereby permitting the relative rotation to take place. Such surfaces are less ergonomic than desired, and do not provide for optimal manipulation by the physician. By providing a thicker and more contoured rotatable valve control member as described, the ergonomics are improved, and the physician can more easily grasp and control the valve device. However, when a thicker valve control member is utilized, relative rotation between the members is inhibited, or prevented entirely, because the increased thickness hinders the ability of the rotatable member to flex. The arrangement described herein enables such relative rotation to occur as a result of the flexure of the outer ridge, and also allows ratcheting action that provides the tactile feedback to the physician.

Rotatable valve control member 16 also includes an inwardly directed snap ring 52 at the distal end thereof. Snap ring 52 is sized and arranged to form a snap fit with external snap ring 34 of valve collar 14. This is best shown in FIG. 3. Rotatable valve control member 16 also includes a snap ring 54 at its proximal end. Snap ring 54 is sized and arranged to fixedly engage a complementary snap ring on end cap 56. Rotatable valve control member 16 and end cap 56 are engaged in a manner such that relative rotation between them is precluded.

Figure 13:
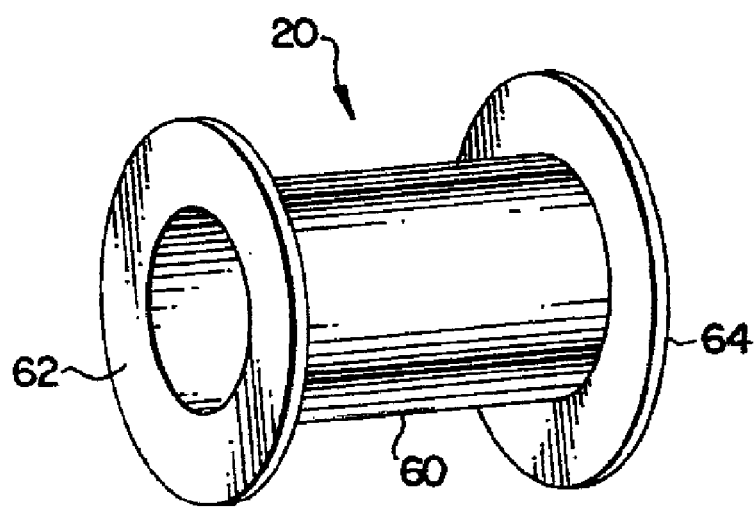
FIG. 13 is a perspective view of the iris valve sheath according to one embodiment of the invention.

FIG. 13 illustrates a preferred embodiment of a flexible valve sheath 20. Sheath 20 comprises a generally cylindrical body 60 having annular flanges 62, 64 disposed at the respective distal and proximal ends of body 60. In the preferred embodiment shown, one of the flanges (in this case proximal flange 64) has a larger diameter, and the other flange (in this case distal flange 62) has a smaller diameter.

Although valve sheath 20 is illustrated in the figures as having a generally cylindrical main body 60, the main body can have other configurations, such as the accordion-like shape and the hour-glass shape illustrated in FIGS. 16 and 17 of the incorporated by reference U.S. Pat. No. 7,172,580. Still other geometrical-shaped cross-sections may be utilized if desired. Non-limiting examples of such shapes include rectangular, triangular or diamond shapes.

Valve chamber 12, valve collar 14, rotatable valve control member 16, collar seal 21, and end cap 56 are preferably formed of a machined or injection molded relatively hard polymeric material, such as acetal, polypropylene, ABS, nylon, PVC, polyethylene or polycarbonate. Those skilled in the art will appreciate that other suitable compositions may be substituted for those identified herein. As illustrated, each of the aforementioned constituents includes a hollowed-out center portion, such that when the device is fully assembled, a passageway is defined to enable passage of an interventional device therethrough.

Valve sheath 20 is preferably elastomeric, and more preferably, is formed of injection molded silicone. A non-limiting list of other suitable materials for use in forming the valve member includes isoprene, latex and various rubber or polymeric compositions. For the purposes of the present invention, the durometer of the valve sheath should be considerably less than the durometer of the body, base and rotatable valve control members, resulting in a valve sheath that is softer and more flexible than the remaining structure. If desired, all of part of the valve sheath may be coated with a lubricious coating, such as parylene or a silicone lubricant (e.g., Dow Coming 360 medical fluid), to improve the lubricity of the surface and facilitate the passage of the device therethrough.

Hemostatic valve assembly 10 may be assembled in the following manner. Initially, valve disks 18 are aligned as described above, and loaded into valve collar large diameter portion 30, or into the hood portion of ring member 28. Valve collar large diameter portion 30 is then engaged with valve chamber 12, e.g., via the snap fit previously described, in a manner such that valve disks 18 are compressed into the space between valve chamber 12 and valve collar 14, as shown in FIG. 3. Ring member 28 provides a fitted surface for receiving disks 18. Preferably, a thin layer of a sealing lubricant, such as RTV silicone, is placed between ring 28 and valve chamber 12 to provide a seal at their interface. In this case, the sealing lubricant acts in the nature of a gasket.

Those skilled in the art will appreciate that valve collar 14 and valve chamber 12 need not be attached by the method described, and other well-known methods of affixation of two parts may be substituted. However, best results are obtained when relative rotation between the two parts is prevented. The insertion and capture of valve disks between two substrates is well-known in the medical arts, and those skilled in the art will appreciate that other suitable ways of capturing these valve disks may be substituted for those described.

Collar seal 21 is fitted over the generally cylindrical body 60 of elastomeric valve sheath 20 by any convenient method, such as by temporarily compressing axial annular flange 64 and passing the temporarily compressed end through aperture 59 in the collar seal. (FIG. 2). Distal flange 62 of valve sheath 20 is axially aligned with valve-receiving surface 15 of valve collar 14. Collar seal 21 is then urged in the distal direction against distal flange 62 toward valve-receiving surface 15. Preferably, valve collar 14 includes slots 25 sized and positioned to mate with corresponding ridges 31 on collar seal 21, to thereby effect a snap fit therebetween. When snapped together, collar seal 21 compresses flange 62 against valve-receiving surface 15, thereby securing flange 62 in valve collar 14 in a manner that prevents flange 62 from rotating, disengaging or otherwise separating from valve collar 14 during conditions of normal use.

Valve collar 14 and rotatable valve control member 16 are engaged by loosely snapping together valve collar snap ring 34 and rotatable valve control member snap ring 52 to establish a loose snap fit therebetween. The engagement of valve collar 14 and rotatable valve control member 16 must be loose enough to allow relative rotation therebetween, but secure enough to prevent disengagement during use. This engagement is best shown in FIG. 3. Those skilled in the art will recognize that other attachment mechanisms may be substituted for the mechanism described, as long as relative rotation is maintained between the valve collar and the rotatable valve control member, and the members are aligned such that they do not disengage during normal use of the device.

Proximal flange 64 of the elastomeric valve member is extracted through central aperture 17 (FIGS. 9, 11) of rotatable valve control member 16 in the proximal direction by any convenient means, such as by pulling flange 64 through the hole with a suitable tool, such as tweezers. With proximal flange 64 resting on rotatable valve control member valve-receiving surface 57, end cap 56 is engaged with rotatable valve control member 16 by, e.g., a snap fit. The snap fits described hereinabove can be accomplished in any convenient fashion, such as by use of a small hand press, or by simply snapping the end cap into place at the proximal end of rotatable valve control member 16. Alternatively, instead of a snap fit, those skilled in the art will appreciate that other engagement means known in the art can be substituted, such as mating screw threads or a friction fit. When the device is assembled, elastomeric valve flange 64 is compressed against valve-receiving surface 57 of rotatable valve control member 16, in a similar manner as the previously-described compression of elastomeric valve flange 62 against the valve-receiving surface 15 of valve collar 14.

If desired, the device can be provided with a mechanism for limiting the amount of rotation of rotatable member 16 relative to collar 14. In the embodiment shown, collar 14 includes a tab 35 that is sized and positioned to engage a corresponding stop 55 of rotatable member 16 for limiting the rotation of rotatable member to an amount less than a fall revolution of 360°. The same mechanism that creates the ratcheting effect helps keep the valve from recoiling and maintain its current position.

Figure 14:
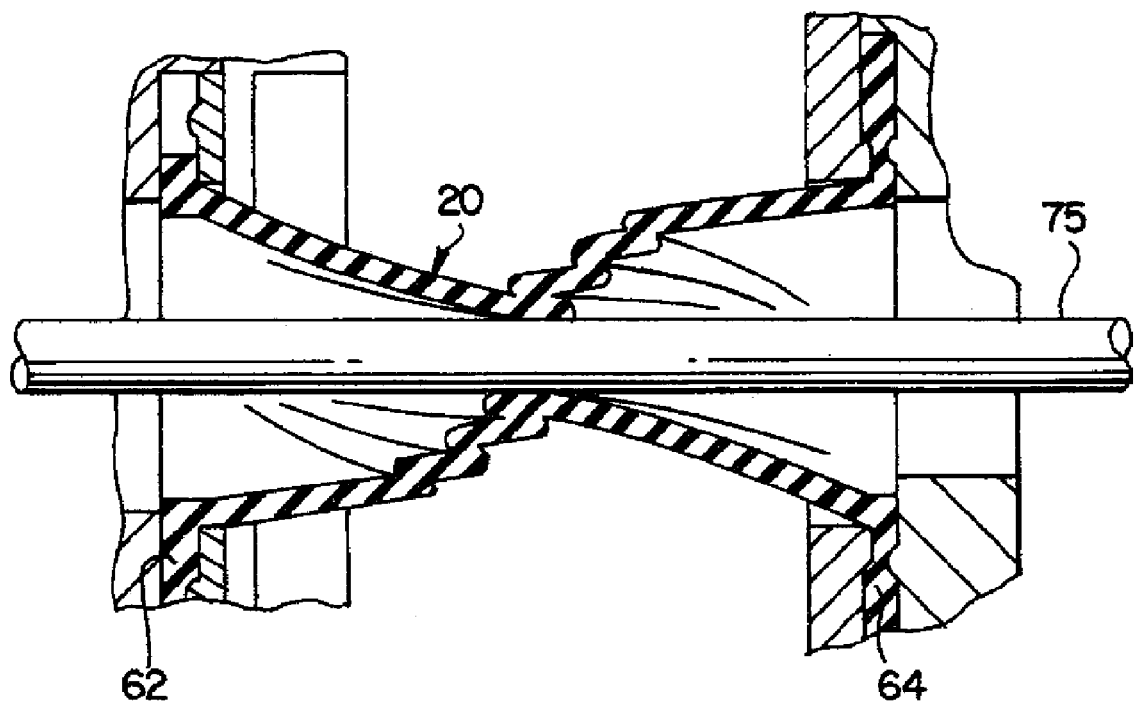
FIG. 14 is a sectional view of the iris valve sheath of FIG. 13, illustrating the valve sheath as it forms a seal around an interventional device.

Operation of the iris valve portion of the hemostatic valve assembly 10 is commenced when the operator grasps rotatable valve control member 16, and rotates this member relative to valve collar 14. Since distal flange 62 and proximal flange 64 of valve sheath 20 are fixedly secured in the respective distal and proximal ends of the valve assembly as described, rotation of valve control member 16 causes an axially intermediate portion (existing between the fixed distal and proximal flanges 62, 64) of the soft polymeric material of the valve member 20 to twist on itself from the opened position shown in the figures to a closed or constricted position. When in this position, the center opening of the valve is twisted, and thereby constricts. FIG. 14 illustrates constriction of the valve member around an interventional device, in this case a dilator 75. When an interventional device is not present, rotatable member 16 may be rotated in a manner to cause the valve to fully close. Constriction of a center passageway of an iris valve in the manner described is known in the art, and is further described and illustrated in the incorporated-by-reference documents. Such constriction results in the formation of a seal between the valve and an interventional device inserted therethrough, or alternatively, in closure of the valve when no interventional device is present.

The iris-type closure utilized in the inventive device provides a particularly effective seal for an introducer sheath or like medical device when catheters or other introducer devices of varying diameters are introduced therein, and also when no catheter is introduced and the lumen of the introducer must be maintained in a closed, leakproof condition. The seal also has a high resistance to tearing when penetrated by large diameter catheters, and is capable of tolerating repeated catheter insertions and withdrawals without any appreciable decrease in performance characteristics of the seal or valve.

Although the preferred embodiment of hemostatic valve assembly 10 of the present invention preferably includes one or more valve disks 18 in combination with valve sheath 20, the presence of a secondary valve source, such as the valve disks, is not necessarily required. In this event, the valve chamber 12 may be omitted, and its features may be combined in a discrete valve collar 14. If desired, valve collar 14 may be shaped or otherwise configured for attachment to an introducer sheath, and/or may include a side arm spout for transmittal or drainage of a fluid or a drug as described. As a still further alternative, a secondary valve source other than valve disks may be provided. Such valves are well known, and those skilled in the art can readily select an alternative valve source to the valve disks illustrated and described herein.

While this invention has been particularly shown and described with reference to preferred embodiments thereof, it will be understood by those skilled in the art that various changes in form and details may be made therein without departing from the spirit and scope of the invention. Those skilled in the art may recognize or be able to ascertain using no more than routine experimentation, many equivalents to the specific embodiments of the invention described specifically herein, which equivalents are intended to be encompassed in the scope of the invention.

The invention claimed is:

1. A valve assembly for controlling a flow of fluid, said valve assembly comprising:
   a valve collar having a proximal end and a distal end, said valve collar structured such that at least a portion of said proximal end is capable of flexure in a radially inward direction, said valve collar portion capable of flexure comprising at least one generally U-shaped cut-out;
   a rotatable valve control member having a proximal end and a distal end, said rotatable valve control member including an ergonomically arranged outer surface, said rotatable valve control member distal end being engaged with said valve collar proximal end in a manner such that said valve control member is at least partially rotatable relative to said valve collar, said rotatable valve control member including a mechanism for engagement with said valve collar portion upon rotation of said rotatable valve control member, said rotatable valve control member and said valve collar aligned to define an elongated passageway; and
   a flexible valve member having a proximal end and a distal end, said valve member distal end being secured to said valve collar, and said valve member proximal end being secured to said rotatable valve control member; said flexible valve member being disposed along said passageway and having a longitudinal opening therethrough;
   wherein upon rotation of said rotatable valve control member in a first direction relative to said valve collar, said mechanism of said rotatable valve control member engages said valve collar portion in a manner such that said valve collar portion flexes in said radially inward direction and a tactile sensation is produced thereby, and such that said flexible valve member longitudinal opening constricts from an open position to a position wherein said opening is at least partially closed.

2. The valve assembly of claim 1, wherein said value collar portion capable of flexure comprises a plurality of generally U-shaped cut-outs.

3. The valve assembly of claim 1, wherein said valve collar portion comprises at least one bridge defined by said U-shaped cut-out, and an outer ridge projecting in a radially outer direction from a terminal end of said bridge.

4. The valve assembly of claim 3, wherein said mechanism of said rotatable valve control member comprises at least one inner member sized and shaped for engagement with said outer ridge.

5. The valve assembly of claim 1, wherein said ergonomically arranged outer surface of said rotatable valve control member comprises a plurality of members projecting radially outwardly from said outer surface.

6. The valve assembly of claim 1, wherein said rotatable valve control member is provided with a gently curved outer contour from a smaller diameter proximal end to a larger diameter distal end.

7. The valve control assembly of claim 6, wherein said rotatable valve control member has a thickness such that flexure of said rotatable valve control member relative to said valve collar during rotation is substantially inhibited.

8. The valve assembly of claim 7, wherein said ergonomically arranged outer surface comprises a plurality of ribs disposed along said outer surface.

9. The valve assembly of claim 7, wherein said mechanism of said rotatable valve control member comprises at least one inner member sized and shaped for engagement with said valve collar portion in a manner such that said valve collar portion is capable of said radially inward flexure during rotation of said valve control member relative to said valve collar for producing a tactile click-type sensation, thereby facilitating said rotation.

10. The valve assembly of claim 1, wherein said ergonomically arranged outer surface of said rotatable valve control member comprises a gently curved outer contour from a smaller diameter proximal end to a larger diameter distal end, and a plurality of ribs disposed along said outer surface.

11. The valve assembly of claim 1, comprising a valve chamber having a proximal end and a distal end, said valve chamber proximal end engaged with said valve collar distal end in a manner such that a passageway is disposed there between, said valve assembly further comprising a secondary valve member disposed in said passageway between said valve chamber and said valve collar.

12. The valve assembly of claim 11, wherein said secondary valve member comprises at least one valve disk.

13. A valve assembly for controlling a flow of fluid, said valve assembly comprising:
   a valve chamber having a proximal end and a distal end;
   a valve collar having a proximal end and a distal end, said valve collar distal end engaged with said valve chamber proximal end, said valve collar comprising at least one generally U-shaped cut-out defining a portion capable of radial flexure, said portion comprising a radial ridge;
   a rotatable valve control member having a proximal end and a distal end, said rotatable valve control member including an ergonomically arranged outer surface, said ergonomically arranged outer surface comprising a gently curved outer contour from a smaller diameter proximal end to a larger diameter distal end, and further comprising one or more external members disposed along said contour for facilitating grasping and control of said rotatable valve control member, said rotatable valve control member distal end being engaged with said valve collar proximal end in a manner such that said valve control member is at least partially rotatable relative to said valve collar, said rotatable valve control member including at least one inner member sized and shaped for engagement with said valve collar ridge in a manner such that said ridge flexes during rotation of said valve control member relative to said valve collar; said valve chamber, valve collar and rotatable valve control member aligned in said valve assembly to define an elongated passageway therethrough; and a flexible valve member having a proximal end and a distal end, said flexible valve member distal end being secured to said valve collar, and said valve member proximal end being secured to said rotatable valve control member; said flexible valve member being disposed along said passageway and having a longitudinal opening therethrough;

wherein upon rotation of said rotatable valve control member in a first direction relative to said valve collar, said at least one inner member of said rotatable valve control member engages a respective valve collar ridge in a manner such that said valve collar portion flexes in a radial direction and a tactile sensation is produced thereby, and such that said valve member longitudinal opening constricts from an open position to a position wherein said opening is at least partially closed.

14. The valve assembly of claim 13, wherein said assembly defines a chamber between said valve chamber and said valve collar, said assembly further comprising a secondary valve member disposed in said chamber.

15. The valve assembly of claim 14, wherein said secondary valve member comprises at least one valve disk.

16. The valve assembly of claim 15, wherein said secondary valve member comprises three valve disks aligned in sequential fashion in said chamber.

17. The valve assembly of claim 13, wherein said one or more external members of said rotatable valve control member comprises a plurality of members projecting radially outwardly from said outer surface.

18. The valve assembly of claim 17, wherein said external members comprise a plurality of ribs disposed along said outer surface.

* * * * *